(12) United States Patent
Ringler et al.

(10) Patent No.: US 7,023,540 B2
(45) Date of Patent: Apr. 4, 2006

(54) METHOD AND APPARATUS FOR RECOGNITION OF COLOR BRIGHTNESS VARIATIONS

(75) Inventors: Ralf Ringler, Neuenstein (DE); Mario Pawlowski, Münchingen (DE)

(73) Assignee: Dr. Ing. h.c.F. Porsche AG, Stuttgart (DE)

( * ) Notice: Subject to any disclaimer, the term of this patent is extended or adjusted under 35 U.S.C. 154(b) by 282 days.

(21) Appl. No.: 10/661,786

(22) Filed: Sep. 15, 2003

(65) Prior Publication Data

US 2004/0119980 A1   Jun. 24, 2004

(30) Foreign Application Priority Data

Sep. 13, 2002   (DE) ................. 102 42 620

(51) Int. Cl.
  *G01N 21/55* (2006.01)
  *G01N 21/88* (2006.01)

(52) U.S. Cl. ............... 356/237.2; 356/237.3; 356/394; 382/141; 250/462.1

(58) Field of Classification Search .. 356/237.1–237.3, 356/394, 445–446, 448, 600–601; 382/141, 382/168; 250/462.1, 463.1; 438/128, 92, 438/94, 125–126; 364/551.01
See application file for complete search history.

(56) References Cited

U.S. PATENT DOCUMENTS

| | | | | |
|---|---|---|---|---|
| 4,918,321 A | * | 4/1990 | Klenk et al. | 250/559.05 |
| 4,989,981 A | * | 2/1991 | Kawamura et al. | 356/394 |
| 5,142,648 A | * | 8/1992 | Fitts et al. | 382/108 |
| 5,160,977 A | * | 11/1992 | Utsumi | 356/606 |
| 5,414,518 A | * | 5/1995 | Yazejian | 356/613 |
| 5,436,726 A | * | 7/1995 | Ventura et al. | 356/613 |
| 5,636,024 A | | 6/1997 | Crookham et al. | |
| 5,686,987 A | | 11/1997 | Hewitt et al. | |
| 5,862,199 A | * | 1/1999 | MacKenzie | 378/89 |
| 6,266,138 B1 | * | 7/2001 | Keshavmurthy | 356/237.2 |
| 6,320,654 B1 | * | 11/2001 | Alders et al. | 356/237.2 |
| 6,398,870 B1 | * | 6/2002 | Kaya et al. | 118/323 |
| 6,532,066 B1 | * | 3/2003 | Filev et al. | 356/237.2 |

FOREIGN PATENT DOCUMENTS

| | | |
|---|---|---|
| DE | 3418317 C1 | 1/1985 |
| DE | 3813239 | 11/1989 |
| DE | 19820536 | 10/1999 |
| DE | 19830745 C1 | 3/2000 |
| DE | 19839882 | 4/2000 |
| DE | 10103555 A1 | 8/2002 |
| EP | 0286994 A2 | 10/1986 |
| WO | WO-9808078 A1 | 2/1998 |

* cited by examiner

Primary Examiner—Gregory J. Toatley, Jr.
Assistant Examiner—Sang H. Nguyen
(74) Attorney, Agent, or Firm—Crowell & Moring LLP

(57) ABSTRACT

In the case of a method and a system for visually detecting paint gloss deviations, particularly a fogginess and mottling of the paint, in a surface paint coat of a vehicle by means of an illuminating system illuminating the vehicle, the outer surfaces of the two vehicle sides as well as additional surfaces of the forward and rearward vehicle body are illuminated by light beaming devices of the illuminating system in a partially areal manner. These surfaces are to be checked at a distance from the vehicle at predefined viewing ranges and from fixed viewing positions on a marked path.

19 Claims, 4 Drawing Sheets

METHOD AND APPARATUS FOR RECOGNITION OF COLOR BRIGHTNESS VARIATIONS

BACKGROUND AND SUMMARY OF THE INVENTION

This application claims the priority of Germany, filed Sep. 13, 2002, the disclosure of which is expressly incorporated by reference herein.

The invention relates to a method and a system for visually detecting deviations in paint gloss according to the preamble of claim 1.

From European Patent Document EP 0 286 994 A2, a method and a system are known for detecting surface defects, preferably for detecting paint defects on the surface of a motor vehicle body. By means of an illuminating system, a streak of light is generated on the surface, and this streak of light is guided by means of a relative movement between the illuminating system and the surface over this surface, and streak-shaped sections of the surface of the objects are in each case recorded in steps in the area of the light streak. Further, from International Patent Document WO 98/08078, a system for the visual inspection of the surface finish of matching surfaces is known, particularly of painted vehicle bodies, by means of several illuminating elements whose main beaming direction extends in each case at slanted angles with respect to the matching surface.

It is an object of the invention to provide an improved method and a system for visually detecting deviations in paint gloss, particularly a fogginess or mottling of the paint of a surface coating of a vehicle.

According to the invention, this object is achieved by means of the method characteristics of claims 1 and 2 as well as by means of the system characteristics according to claims 3 to 12.

The principal advantages achieved by means of the invention are that a visual detection of irregularities of the vehicle paint coat takes place as early as in the initial stage and corresponding correction measures can be taken for eliminating the defects. For the visual detection of these irregularities, such as fogginess and mottling of the paint, the outer surfaces of the two vehicle sides as well as additional surfaces of the forward and rearward vehicle body are illuminated by beams of light in a partially areal manner and, at a distance from the vehicle at predefined viewing ranges and defined viewing positions, these surfaces are judged on a marked path. The marked path consists of a semicircle on the lateral surfaces of the vehicle and an adjoining segment of a circle on the forward and rearward vehicle body. On this path, the viewing positions are assigned to the light beaming devices, in which case, additional positions for looking at the vehicle surfaces exist between the viewing positions on the marked path. As a result, it is advantageously achieved that the fogginess and the mottling respectively of the paint can be detected at all. The reason is that it is not only the illumination which is decisive but also the judging distance and the viewing positions with respect to the vehicle. Only when the entire surface to be judged can be seen as a whole, can the fogginess and mottling in the surface of the vehicle body be detected.

It was found that, because of the physical conditions, the amount of paint which can be sprayed onto vertical surfaces (for example, doors) is always less than the amount which can be sprayed onto horizontal surfaces (for example, the hood). As a result of the insufficient layer thickness of the coloring paint (base paint), fogginess and mottling will then be visible mainly on the sides of the vehicle body. In normally illuminated factory hangars, paint shop lines and even at well illuminated test sites, vehicle bodies with foggy and mottled paint coats can hardly be detected.

In order to remedy this condition, the light beaming devices are arranged at a distance with respect to both sides of the vehicle, in each case, in the longitudinal vehicle center plane for the lateral vehicle surfaces and in the transverse vehicle center plane for the forward and rearward vehicle body. The viewing positions are arranged on the marked path directly behind the light beaming devices in the transverse vehicle center plane, and the additional viewing positions for the light beaming devices assigned to the forward and rearward vehicle body are provided in the longitudinal vehicle center plane in each case on both sides of these light beaming device on the path. In particular, the light beam of the respective light beaming device should impinge approximately in the center of the forward and rearward vehicle body respectively as well as of the lateral vehicle surfaces, and the light cones of the light beaming devices comprise the entire length of the lateral vehicle surfaces and that of the forward and rearward vehicle body. The viewing range from the lateral viewing positions on the marked path, on the one hand, (word missing—translator) onto the entire lateral vehicles surfaces and, on the other hand, these viewing ranges overlap with the viewing ranges from the forward and rearward viewing positions on the forward and rearward vehicle body.

As a result, it is achieved that, on the one hand, by way of a light beaming device of each vehicle side, which in each case is arranged in the center, as well as on the forward and rearward body structure of the vehicle, first the entire surface to be judged is illuminated and can be viewed from predetermined viewing positions. When assessing paint surfaces on vehicle bodies, it was found that even slight parameter deviations at certain light conditions prove to be a serious defect. For example, if the door filler paint coat was machined (ground) because of a dust particle and subsequently the coloring base paint (for example, silver metallic) has a smaller layer, a light spot will appear in the door later when subjected to direct sun radiation. If the layer thickness is much too low, the spot will be clear and strong at its edges. When there is only a slightly smaller underlayer, the edges of the ground paint will be indistinct and therefore harder to be discerned by the customer.

For the further partial judging of the paint surface of the vehicle sides as well as of the forward and rearward vehicle body, two light beaming devices are provided for each vehicle side, whose cones of light overlap on the lateral surfaces, and the lateral vehicle surface as well as the surfaces of the forward and rearward vehicle body can be illuminated to the longitudinal center plane of the vehicle. The viewing positions are the same as in the case of only one light beaming device, these being provided on the marked path for each vehicle side in each case behind the two light beaming devices in the transverse vehicle center plane, and the viewing range in each case extending along a partial area of the lateral surface and overlapping with the viewing ranges from the forward and rearward viewing positions on the lateral surfaces.

So that an exact illumination of the vehicle surface to be assessed can take place, the light beaming devices for the lateral vehicle surfaces are aligned such that the light beam is oriented approximately at an angle of 90° with respect to the ground surface and impinges laterally on the surface to be checked, and the light cone extends in the vertical direction approximately from the vehicle side member to the belt line of the vehicle. The light beaming device on the rearward and forward vehicle body is aligned such that the light cone is aligned approximately in the center at an angle with respect to the ground surface and, in the case of the rearward vehicle body impinges in the vertical direction on an upward-curved area of the rear part, and the light cone covers (something is missing in the German—translator) in the lower edge of the rear window. In the case of the forward vehicle body, the line cone comprises the forward hood area in the vertical direction.

By means of the invention, an assessment of the fogginess and mottling takes place according to a defined standardized method with defined system elements, such as a illuminating system. For the assessment, it is provided according to the invention that, on the one hand, the viewing positions are defined on the marked path and, on the other hand, the judging person walks at a defined distance on the path around the vehicle in order to check the surface to be assessed.

In principle, the judging of the fogginess/mottling does not take place exclusively from one or more viewing positions but (the fogginess/mottling? translator) becomes more conspicuous when the person making the assessment is moving. Fogginess and spots in a paint coat occur only in the case of metallic paint coats. The conspicuous shadings result from metal particles (called bronze) situated in different directions. If one now moves along a vehicle body painted in a foggy/mottled manner, the conspicuousness rises many times over because the human eye subconsciously perceives mainly the light/dark change. One of the reasons why a movement should take place during the assessment is the fact that only extreme fogginess can be shown photographically. In contrast, the producing of a video film, like a movement, permits the recording of even slight fogginess/mottling.

So that an optimal judging of the fogginess/mottling can take place, not only the setup and sequence of the checking, but also a categorization according to a so-called ten scale is important. Since, during the checking, a certain subjectivity should still be considered, it is recommended that the checking be carried out by a team of experts. This means in practice that at least three experts from the fields of production, finishing and quality assurance judge individually and subsequently the individual results are used to take the average.

The ten scale describes the assessment categories, Point 1 being a good value and Point 10 being a poor value:

(1) No fogginess/mottling can be detected;
(2) only a very slight graining of the paint coat can be detected;
(3) homogeneous indistinct graining can be detected;
(4) uniform graining can be detected in the paint coat;
(5) slight shading or light indistinct spots can be detected;
(6) extreme shading or clearly defined spots can be detected (defect images of Steps 6 to 10 are relevant with respect to refinishing and customers);
(7) easily detectable shading or clearly defined spots; defects can be recorded photographically;
(8) shading or spots which are difficult to detect in neon light (2,000 lux);
(9) shading or spots which can easily be detected in neon light (2,000 lux);
(10) shading/spots which are immediately conspicuous in neon light (2,000 lux).

An embodiment of the invention is illustrated in the drawings and will be described in detail in the following.

DETAILED DESCRIPTION OF THE PREFERRED EMBODIMENTS

Figure 1:
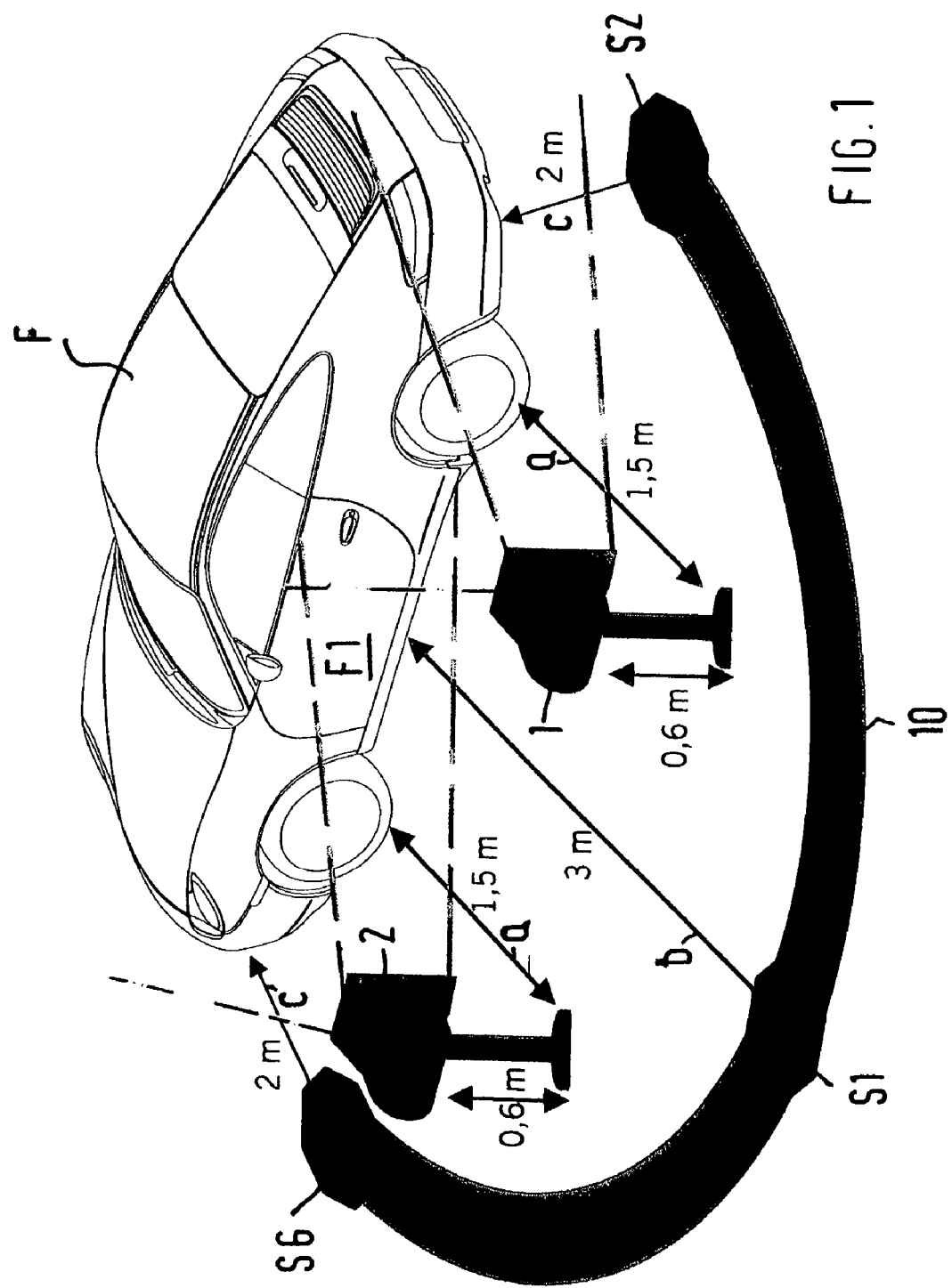
FIG. 1 is a diagrammatic representation of a checking site with a marked path and fixedly placed light beaming devices.
Figure 2:
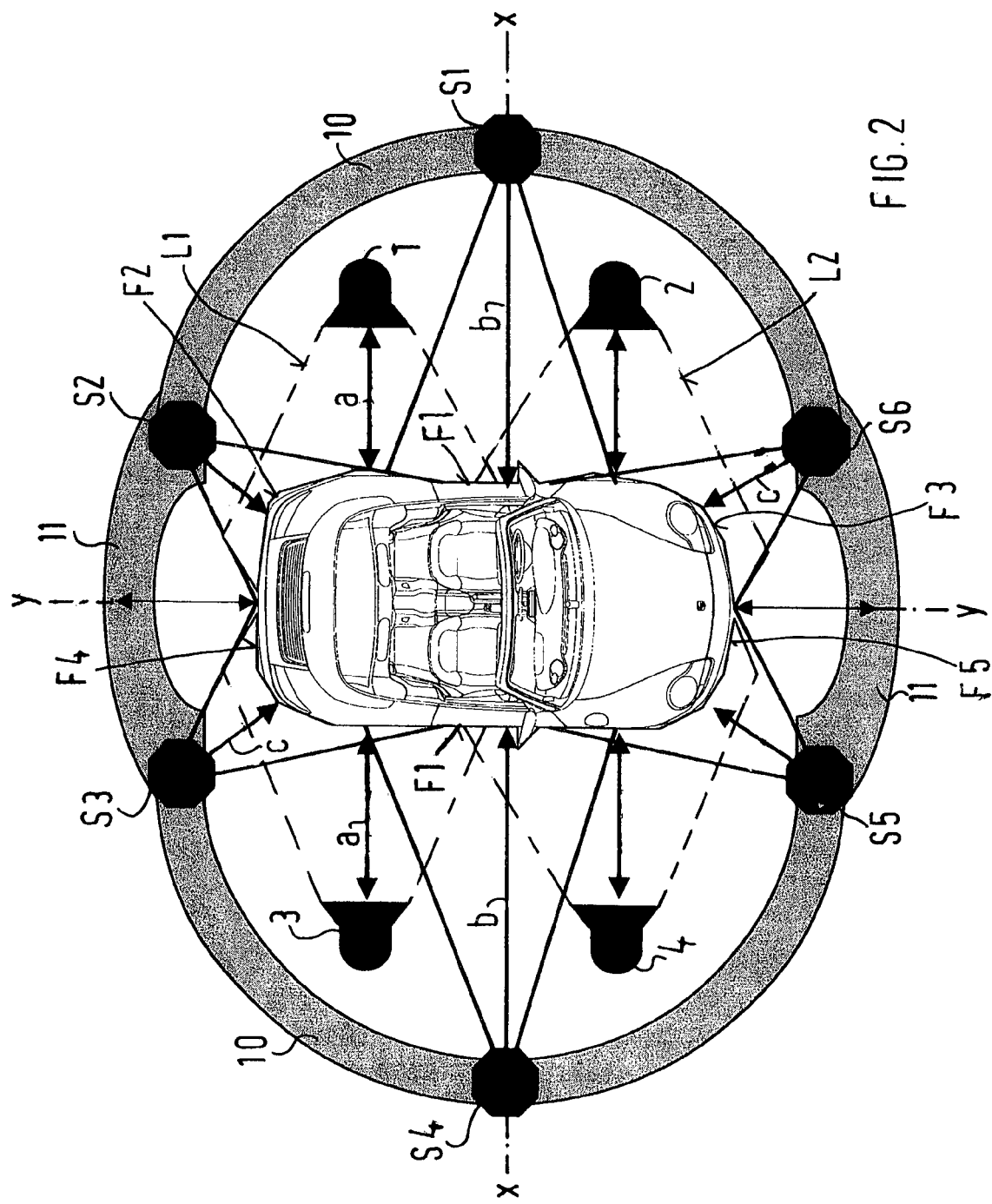
FIG. 2 is a top view of a checking site with a marked path and two light beaming devices respectively on each lateral vehicle surface.
Figure 3:
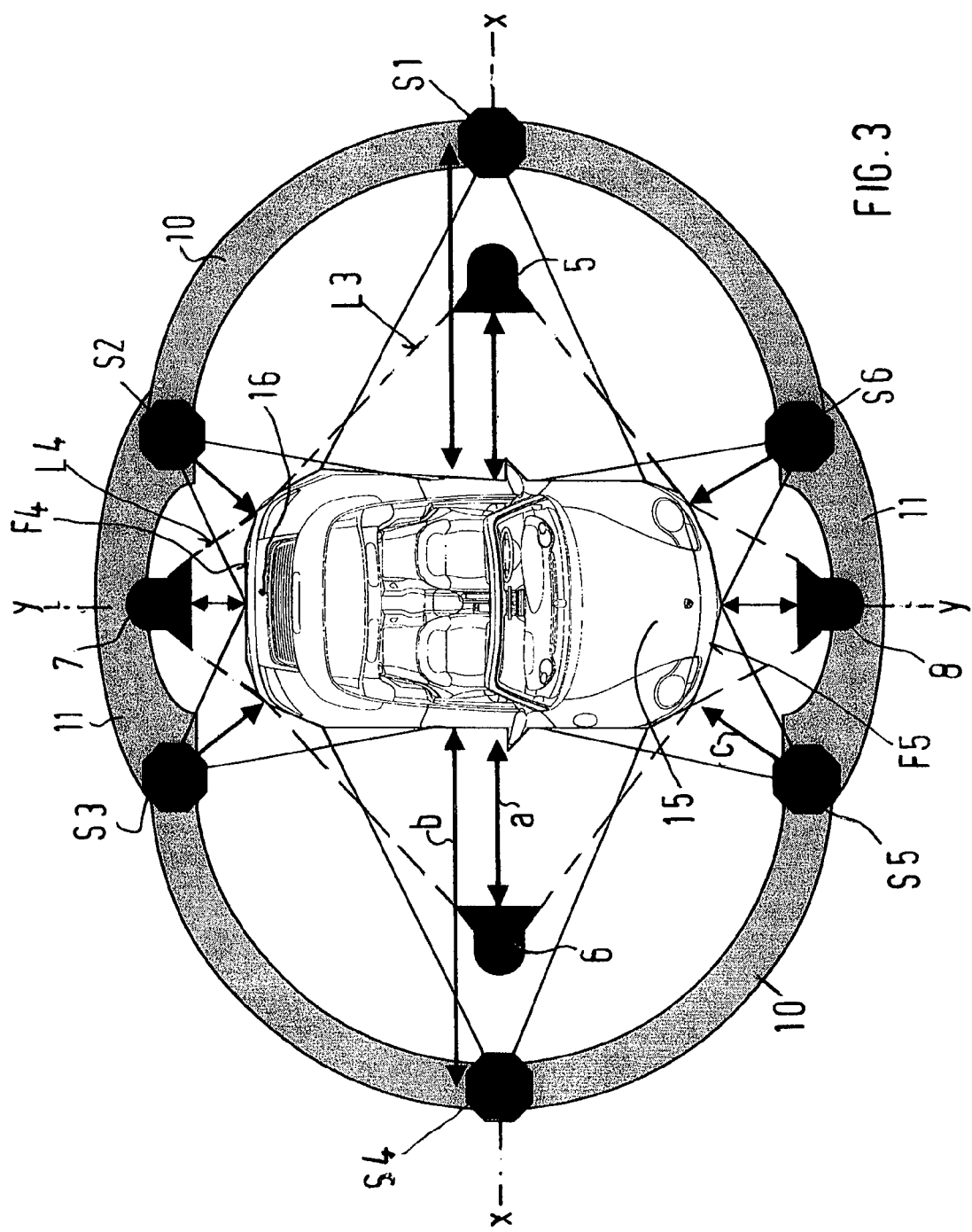
FIG. 3 is a top view of the checking site with a marked path and one light beaming device respectively on the lateral surfaces of the vehicle and as well one light beaming device respectively on the forward and rearward vehicle body.

Fixedly positioned light beaming devices 1, 2, 3 and 4 according to FIGS. 1 and 2 and fixedly positioned light beaming devices 5, 6, 7 and 8 according to FIG. 3 are provided for judging the paint surfaces on vehicle bodies. These light beaming devices are arranged within a marked path 10, 11, different viewing positions S1 to S6 for an observer being arranged on this path 10, 11.

As illustrated in FIG. 1, the distances of the light beaming devices from the vehicle F are fixed at a distance a=1.5 m. The viewing positions S1 and S4 on the path 10 are fixed at a distance b=3 m from the vehicle F, the viewing positions S2, S3, S5 and S6 being provided at a distance c=2 m with respect to the vehicle.

The marked path 10, which is in each case arranged at a distance laterally of the vehicle F, is constructed as a semicircle and changes into another arc 11 in front of and behind the vehicle. According to FIG. 2, the viewing positions S1 and S4 are provided on these paths 10, 11 approximately in the transverse vehicle center plane X—X, the light beaming devices 1, 2 and 3, 4 each being arranged at a short distance a from the vehicle on both sides of the transverse vehicle center plane X—X. The light cones L1 and L2 of the light beaming devices 1, 2 overlap on the lateral vehicle surface F1.

The viewing ranges from the viewing positions S1 and S2 or S6 supplement one another such that the entire lateral surface F1 as well as a rear area with the surface F2 and a frontal area with the surface F3 are covered to the longitudinal vehicle center plane Y—Y for the observation.

In the embodiment according to FIG. 3, the viewing positions S1 to S6 are implemented identically with the viewing positions according to FIG. 2. The light beaming devices 5,6 facing the lateral surfaces F1 of the vehicle F are arranged approximately in the transverse vehicle center plane X—X, in which case the light beaming devices 5 and 6 illuminate the entire length of the lateral surface Fl of the vehicle F. In the longitudinal center plane Y—Y, the light beaming devices 7, 8 are arranged at a distance a with respect to the vehicle F and have a light cone L4 which intersects with the light cone L3 of the light beaming device 5, 6 in the corner area of the vehicle F. The viewing ranges from the viewing positions S1 and S2 overlap so that a surface-covering observation of the vehicle body surfaces is ensured.

Figure 4:
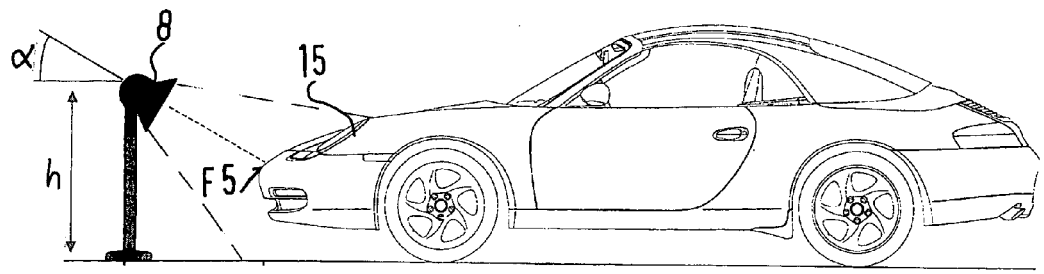
FIG. 4 is a lateral view of the vehicle with a light beaming device assigned to the forward vehicle body.
Figure 5:
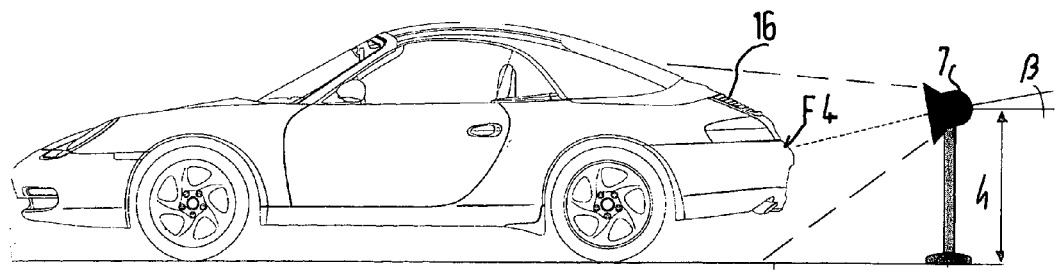
FIG. 5 is a lateral view of the vehicle with a light beaming device assigned to the rearward vehicle body.
Figure 6:
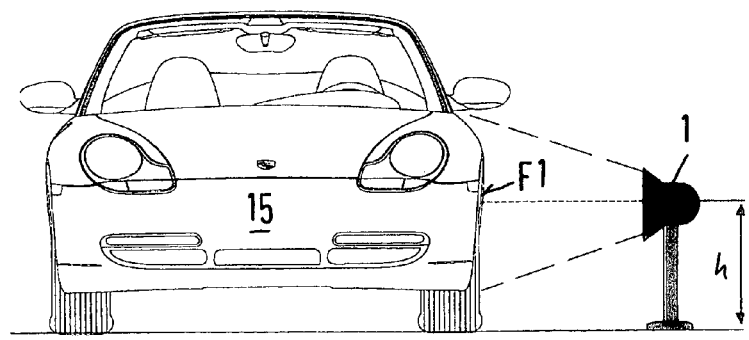
FIG. 6 is a frontal view of the vehicle with a light beaming device directed at a vehicle side.

FIG. 4 shows the light beaming device 8 for the forward vehicle body 15 which is arranged at a height h=0.6 m and is sloped at an angle of $^\triangle$=20° with respect to the contact surface of the tire, and the light cone illuminates a portion of the vehicle hood in the vertical direction. Correspondingly, the light beam L4 for the vehicle rear 16 is sloped at an angle $^\triangle$=15° with respect to the ground, and the light cone extends in the vertical direction approximately to the bottom edge of the rear window. In the case of the light beaming device 5 for the vehicle side wall, the light cone extends in the vertical direction to the belt line of the vehicle.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Method for visually detecting paint gloss deviations, particularly a fogginess and mottling of the paint in a surface paint coat of a vehicle by means of an illuminating system illuminating the vehicle, comprising the steps:
   illuminating outer surfaces (F1) of two sides of the vehicle as well as additional surfaces (F3, F5 and F2, F4) of a forward and rearward vehicle body portion by light beaming devices of an illuminating system in a partially areal manner; and,
   observing said outer surfaces and said additional surface along at least one marked path, said observing occurring at a distance (a) from the vehicle (F) at predefined viewing ranges and defined viewing positions (S1 to S6) wherein the at least one marked path consists of a semicircle around the lateral surfaces (F1) of the vehicle and an adjoining segment of a circle to the forward and rearward vehicle body and, on said at least one path, the defined viewing positions (S1 to S6) are assigned to the light beaming devices, and wherein there are additional positions for looking at the outer and additional vehicle surfaces (F1 to F5) between said defined viewing positions (S1 to S6) on one of said at least one marked path.

2. System for implementing the method according to claim 1, said system comprising an arrangement of each of the light beaming devices at a distance from both sides of the vehicle (F) in a longitudinal vehicle center plane (Y—Y) for the lateral vehicle surface (F1), and approximately in a transverse vehicle center plane (X—X) for the forward and rearward vehicle body portions.

3. System according to claim 2, wherein a light beam of the respective at least two other light beaming device impinges approximately in the center of the forward and rearward vehicle body as well as of the lateral vehicles surfaces (F1), and wherein light cones (L3 and L4) of the each of said light beaming devices include the entire length of the outer vehicle surfaces and at least two of the additional surfaces of the forward and rearward vehicle body.

4. System according to claim 3, wherein a viewing range from each lateral viewing positions (S1, S4) on the marked path supplement each other to cover the entire lateral vehicle surface and overlap one another with the viewing ranges from the forward ones of viewing positions (S5 and S6) and the rearward ones of the viewing positions (S2 and S3) onto the forward and rearward vehicle body.

5. System for implementing the method according to claim 2, said system comprising:
   an arrangement of at least one of said defined viewing positions on the marked path directly behind at least two of the light beaming devices in the transverse center plane (X—X) of the vehicle, and
   an arrangement of the additional viewing positions for at least two other of the light beaming devices which are assigned to the forward and rearward vehicle body part, said additional view positions arranged in a longitudinal vehicle center plane in each case on both sides of said at least two other light beaming devices on one of said at least two marked paths.

6. System for implementing the method according to claim 1, said system comprising:
   an arrangement of at least one of said defined viewing positions on the marked path directly behind at least two of the light beaming devices in the transverse center plane (X—X) of the vehicle, and
   an arrangement of the additional viewing positions for at least two other of the light beaming devices which are assigned to the forward and rearward vehicle body part, said additional view positions arranged in a longitudinal vehicle center plane in each case on both sides of said at least two other light beaming devices on one of said at least two marked paths.

7. System according to claim 6, wherein a viewing range from each lateral viewing positions (S1, S4) on the marked path supplement each other to cover the entire lateral vehicle surface and overlap one another with the viewing ranges from the forward ones of the viewing positions (S5 and S6) and the rearward ones of the viewing positions (S2 and S3) onto the forward and rearward vehicle body.

8. System for implementing the method according to claim 1, said system comprising:
   an arrangement of two mutually spaced light beaming devices on each lateral surface (F1) of the vehicle (F), said two spaced light beaming devices having light cones (L1, L2) which mutually intersect on the lateral surface (F1), and
   illumination means for illuminating the outer vehicle surface as well as at least two of said additional surfaces (F4 and F5) of the forward and rearward vehicle body along a longitudinal vehicle center plane (Y—Y).

9. System according to claim 8, wherein the viewing positions (S1, S4) on the marked path for each vehicle side are in each case provided between the two of said light beaming devices approximately in a transverse vehicle center plane (X—X), and the viewing range, in each case, extends over a partial area of the lateral surface (F1) and intersects with the viewing ranges from the forward and rearward ones of said viewing positions on the lateral surfaces (F1).

10. System according to claim 1, wherein the light beaming devices for the forward vehicle surface (F5) are aligned such that the light beam is aligned approximately at an angle of 20° with respect to the ground and impinges in a center on a surface to be checked.

11. System according to claim 1, wherein the light beaming device for the rearward vehicle surface (F4) is aligned such that a light cone is aligned approximately in the center at an angle of 15° with respect to the ground and, in the vertical direction, impinges on a upward-curved area of the rear part, and the light cone covers the lower edge of the rear window.

12. System according to claim 1, wherein the light beaming device on the forward vehicle body is aligned such that a light cone impinges in the vertical direction on the upward-curved area of the forward part, and the light cone partially covers the vehicle hood.

13. System according to one claim 1, wherein laterally arranged ones of said light beaming devices are aligned at an angle of 90° with respect to the ground, and a light cone extends in the vertical direction approximately from vehicle side member to a belt line of the vehicle (F).

14. System for implementing the method according to claim 1, said system comprising an arrangement of each of the light beaming devices at a distance from both sides of the vehicle (F) in a longitudinal vehicle center plane (Y—Y) for the lateral vehicle surface (F1), and approximately in a transverse vehicle center plane (X—X) for the forward and rearward vehicle body portions.

15. System for implementing the method according to claim 1, said system comprising an arrangement of two mutually spaced light beaming devices on each lateral surface (F1) of the vehicle (F), said two spaced light beaming devices having light cones (L1, L2) which mutually intersect on the lateral surface (F1), and illumination means for illuminating the outer vehicle surface as well as at least two of said additional surfaces (F4 and F5) of the forward and rearward vehicle body along a longitudinal vehicle center plane (Y—Y).

16. System according to claim 1, wherein the light beaming devices for the forward vehicle surface (F5) are aligned such that the light beam is aligned approximately at an angle of 20° with respect to the ground and impinges in a center on a surface to be checked.

17. System according to claim 1, wherein the light beaming device for the rearward vehicle surface (F4) is aligned such that a light cone is aligned approximately in the center at an angle of 15° with respect to the ground and, in the vertical direction, impinges on a upward-curved area of the rear part, and the light cone covers the lower edge of the rear window.

18. System according to claim 1, wherein the light beaming device on the forward vehicle body is aligned such that a light cone impinges in the vertical direction on the upward-curved area of the forward part, and the light cone partially covers the vehicle hood.

19. System according to one claim 1, wherein laterally arranged ones of said light beaming devices are aligned at an angle of 90° with respect to the ground, and a light cone extends in the vertical direction approximately from a vehicle side member to a belt line of the vehicle (F).

* * * * *